United States Statutory Invention Registration [19]

[11] Reg. Number: H50

Surapaneni et al.

[45] Published: Apr. 1, 1986

[54] PROCESS FOR PREPARING 1,3,5,7-TETRAACETYLOCTAHYDRO-1,3,5,7-TETRAZOCINE

[75] Inventors: C. Rao Surapaneni, Long Valley; Nathaniel S. Gelber, Morristown, both of N.J.

[73] Assignee: The United States of America as represented by the Secretary of the Army, Washington, D.C.

[21] Appl. No.: 762,605

[22] Filed: Aug. 5, 1985

Related U.S. Application Data

[63] Continuation of Ser. No. 562,351, Dec. 16, 1983, abandoned.

[51] Int. Cl.[4] ..... C07D 257/02
[52] U.S. Cl. ..... 260/239 BC; 260/239 HM
[58] Field of Search ..... 260/239

[56] References Cited

U.S. PATENT DOCUMENTS 3,979,379 9/1976 Siele ..... 260/239 HM

OTHER PUBLICATIONS

Siele et al., Propellants and Explosives, 6, (1981) pp. 67–73.

*Primary Examiner*—John F. Terapane
*Assistant Examiner*—Jack Thomas
*Attorney, Agent, or Firm*—Anthony Lane; Robert Gibson; Edward Costigan

[57] ABSTRACT

1,3,5,7-Tetraacetyloctahydro-1,3,5,7-tetrazocine is produced in improved yield by reacting 1,5-diacetyl-1,3,5,7-tetraazabicyclo-[3.3.1]-nonane with acetic anhydride in the presence of a metal acetate, such as sodium acetate.

3 Claims, No Drawings

A statutory invention registration is not a patent. It has the defensive attributes of a patent but does not have the enforceable attributes of a patent. No article or advertisement or the like may use the term patent, or any term suggestive of a patent, when referring to a statutory invention registration. For more specific information on the rights associated with a statutory invention registration see 35 U.S.C. 157.

PROCESS FOR PREPARING 1,3,5,7-TETRAACETYLOCTAHYDRO-1,3,5,7-TETRAZOCINE

The invention described herein may be manufactured, used and licensed by or for the Government for Governmental purposes without payment to us of any oyalties thereon.

This application is a continuation of Ser. No. 562,351, filed Dec. 16, 1983, now abandoned.

BACKGROUND OF THE INVENTION

This invention relates to an improved process for preparing TAT (1,3,5,7-tetraacetyloctahydro-1,3,5,7-tetrazocine) which is an intermediate in a process for preparing the important military explosive HMX (1,3,5,7-tetranitro-1,3,5,7-tetraazacyclooctane).

TAT has been prepared by reacting DAPT (3,7-diacetyl-1,3,5,7-tetraazabicyclo-[3.3.1]-nonane with acetyl chloride, acetic anhydride and sodium acetate (U.S. Pat. No. 3,979,379; Siele et al. "Propellants and Explosives 6, 67 (1981). TAT has also been prepared by heating DAPT with acetic anhydride alone for 3 hours at 110° C. (Propellants and Explosives, loc. cit.) The latter procedure has the important advantage of not requiring the use of acetyl chloride, which is costly and highly corrosive, but the yield of TAT obtained thereby (about 70% of theory) is inferior.

SUMMARY AND DETAILED DESCRIPTION OF THE INVENTION

We have discovered that the yield of TAT obtained by reacting DAPT with acetic anhydride in the absence of acetyl chloride can be significantly increased by carrying out the reaction in the presence of a metal acetate.

The process of the present invention can be carried out by heating a mixture of DAPT, acetic anhydride and metal acetate to produce TAT, and separating the TAT from the reaction mixture. The reaction mixture can be filtered to remove any solid metal acetate present, and the filtrate diluted with water to convert unreacted acetic anhydride to acetic acid. The acetic acid can be removed by vacuum distillation and the TAT can be crystallized from the distillation residue by treatment with a solvent, such as ether.

Theoretically, two mols of acetic anhydride per mol of DAPT are required to form TAT. However, the yield of TAT obtained in the process of the present invention is improved by employing an excess of acetic anhydride over that theoretically required, preferably using about from 5 to 10 mols of acetic anhydride per mol of DAPT. Still greater quantities of acetic anhydride, e.g. 20 mols of acetic anhydride per mol of DAPT, can be effectively employed, but they do not generally result in any further improvement in the yield of TAT.

The reaction of the present invention is preferably carried out at a temperature ranging between about 100° C. and about 125° C., although temperatures outside this range can be employed. However, at lower temperatures the reaction rate is relatively slow while at higher temperatures the reaction leads increasingly to undesired by-products and lower yields of TAT.

A small amount of metal acetate, e.g. as low as 0.01 mol per mol of DAPT, is sufficient to improve the yield of TAT according to the process of the present invention. Preferably, as illustrated in the examples below, the quantity of metal acetate employed corresponds approximately to the amount that can be dissolved in the reaction mixture; additional undissolved metal acetate appears to be ineffective to provide any further advantage and can be recovered by filtration from the reaction mixture. Suitable metal acetates include alkali metal acetates, e.g. sodium-, potassium- and lithium acetates, and alkaline earth metal acetates, e.g. calcium- and magnesium acetates. In lieu of adding the metal acetate to the reaction mixture, an equivalent amount of a metal oxide, -hydroxide or -carbonate can be added, which are believed to react with the acetic anhydride/acid present to form the corresponding metal acetate.

The following examples illustrate specific embodiments of the method of carrying out the process of the present invention.

EXAMPLE 1.

A mixture of 40 ml (0.42 mol) acetic anhydride, 200 mg (0.0024 mol) anhydrous sodium acetate and 10 grams (0.047 mol) DAPT was heated with agitation at 110° C. for 3 hours. The hot reaction mixture was vacuum filtered, and the filtrate was cooled to room temperature, diluted with 15 ml water and concentrated on a rotary evaporator under reduced pressure at about 70° C., leaving a residue of about 20 ml of clear, thick orange-yellow liquid. 50 ml ethyl ether was added to the residue and the resulting mixture was allowed to stand overnight with occasional swirling, whereby TAT was precipitated as a solid. The ether solution was removed by decantation from the solid, which was then triturated with 10 ml acetone and filtered. The filter cake was washed with a small amount of acetone and dried to constant weight, yielding 11.1 g TAT, m.p. 158°-161° C., corresponding to 82.4% of theory yield. The combined decanted ether solution and acetone filtrate was vacuum distilled to remove the solvents, yielding a similar orange liquid, which was processed in the foregoing manner, yielding 0.6 g TAT. The total yield of TAT thus obtained was 11.7 g., corresponding to 86.6% of theory yield.

When the foregoing example was repeated except that the sodium acetate was omitted, the total yield of TAT was 73.2% of theory, obtained in four crops as follows: 7.7 g (57.3%), 1.4 g (10.3%), 0.6 g (4.5%) and 0.2 g (1.1%). Thus, by carrying out the reaction in the presence of sodium acetate, the yield of TAT is substantially increased and the isolation of the TAT is simplified by reduction of the number of crops.

EXAMPLE 2.

The procedure of Example 1 was repeated except that 20 ml (0.21 mol) instead of 40 ml acetic anhydride and 100 mg (0.0012 mol) instead of 200 mg sodium acetate were employed while using the same amount of DAPT. The yield of TAT isolated in the foregoing manner was 11.0 g (82.1% of theory). The first crop of TAT amounted to 9.6 g (72.0%) of theory yield.

When the example was repeated but omitting the sodium acetate, the yield of TAT was 7.4 g (55.6% of theory), of which only 6.3 g (46.9%) were obtained as the first crop.

EXAMPLE 3.

The procedure of Example 1 was repeated except that the sodium acetate was replaced by an equal weight (200 mg=0.002 mol) of potassium acetate. The yield of TAT thus obtained was 12.0 g corresponding to 89.4% of theory.

We claim:

1. The process for producing 1,3,5,7-tetraacetyloctahydro-1,3,5,7-tetrazocine which consists of reacting, in ratio, 1 mol of 3,7-diacetyl-1,3,5,7-tetraazabicycleo[3.3.1]-nonane with at least 5 mols of acetic anhydride in the presence of an alkali metal acetate at a temperature of 100° C. to 150° C., said metal acetate being the maximum amount soluble in the reaction mixture.

2. The process of claim 1 wherein the metal acetate is sodium acetate.

3. The process of claim 1 wherein the metal acetate is potassium acetate.

* * * * *